United States Patent
Ban et al.

(10) Patent No.: US 9,429,575 B2
(45) Date of Patent: Aug. 30, 2016

(54) DNA APTAMER SPECIFICALLY BINDING TO EN2 (ENGRAILED-2) AND USE THEREOF

(71) Applicant: POSTECH ACADEMY-INDUSTRY FOUNDATION, Gyeongsangbuk-do (KR)

(72) Inventors: Changill Ban, Gyeongsangbuk-do (KR); Yoon-Keun Kim, Seoul (KR); Hunho Jo, Busan (KR); Seonghwan Lee, Gyeonggi-do (KR); Hyung Jun Youn, Seoul (KR)

(73) Assignee: Postech Academy-Industry Foundation, Gyeongsangbuk-do (KR)

( * ) Notice: Subject to any disclaimer, the term of this patent is extended or adjusted under 35 U.S.C. 154(b) by 0 days.

(21) Appl. No.: 14/933,113

(22) Filed: Nov. 5, 2015

(65) Prior Publication Data
US 2016/0187342 A1    Jun. 30, 2016

(30) Foreign Application Priority Data

Dec. 24, 2014 (KR) .................. 10-2014-0188124

(51) Int. Cl.
  *C12N 15/11* (2006.01)
  *G01N 33/574* (2006.01)
  *C12N 15/115* (2010.01)

(52) U.S. Cl.
  CPC ....... *G01N 33/57434* (2013.01); *C12N 15/115* (2013.01); *C12N 2310/16* (2013.01); *G01N 2333/47* (2013.01)

(58) Field of Classification Search
  None
  See application file for complete search history.

(56) References Cited

U.S. PATENT DOCUMENTS

2010/0093558 A1    4/2010    Pandha et al.

FOREIGN PATENT DOCUMENTS

| JP | 2009-540852 A | 11/2009 |
|----|---|---|
| JP | 2012-254074 A | 12/2012 |
| WO | 2008/003656 | 1/2008 |
| WO | 2013/085483 | 6/2013 |

OTHER PUBLICATIONS

Velonas et al., "Current Status of Biomarkers for Prostate Cancer," *Int. J. Mol. Sci.*, 2013, vol. 14, No. 6, pp. 11034-11060.
Morgan et al., "Engrailed-2 (EN2): A Tumor Specific Urinary Biomarker for the Early Diagnosis for Prostate Cancer," *Clin Cancer Res*, 2011, vol. 17, No. 5, pp. 1090-1098.
Killick et al, "Role of Engrailed-2 (EN2) as a prostate cancer detection biomarker in genetically high risk men," *Sci Rep*, 2013, 3:2059.
Lee et al., "Cationic Surfactant-Based Colorimetric Detection of *Plasmodium* Lactate Dehydrogenase, a Biomarker for Malaria, Using the Specific DNA Aptamer," PLoS One, Jul. 2014, vol. 9, No. 7, e100847.

*Primary Examiner* — Tracy Vivlemore
*Assistant Examiner* — Kate Poliakova-Georgantas
(74) *Attorney, Agent, or Firm* — Riverside Law LLP

(57) ABSTRACT

The present invention relates to a DNA aptamer specifically binding to EN2 (Engrailed-2), a biosensor for diagnosing prostate cancer having the same, and a method of diagnosing prostate cancer. A strong binding force and excellent specificity of the DNA aptamer of the present invention and the biosensor using the same with respect to EN2 proteins were identified. A detection specificity problem of a prostate-specific antigen (PSA) test used for prostate cancer diagnosis of the related art was addressed. Therefore, the present invention is expected to be beneficially used for early diagnosis of prostate cancer more effectively and increase diagnostic accuracy.

5 Claims, 13 Drawing Sheets

```
                         SEQUENCE LISTING

<160> NUMBER OF SEQ ID NOS: 11

<210> SEQ ID NO 1
<211> LENGTH: 31
<212> TYPE: DNA
<213> ORGANISM: Artificial Sequence
<220> FEATURE:
<223> OTHER INFORMATION: EN2 forward primer

<400> SEQUENCE: 1
cccggatcca tggaggagaa tgaccccaag c                                   31

<210> SEQ ID NO 2
<211> LENGTH: 29
<212> TYPE: DNA
<213> ORGANISM: Artificial Sequence
<220> FEATURE:
<223> OTHER INFORMATION: EN2 Reverse primer

<400> SEQUENCE: 2
cccctcgagc tactcgctgt ccgacttgc                                      29

<210> SEQ ID NO 3
<211> LENGTH: 14
<212> TYPE: DNA
<213> ORGANISM: Artificial Sequence
<220> FEATURE:
<223> OTHER INFORMATION: dsDNA forward

<400> SEQUENCE: 3
cgtgtaatta cctc                                                      14

<210> SEQ ID NO 4
<211> LENGTH: 14
<212> TYPE: DNA
<213> ORGANISM: Artificial Sequence
<220> FEATURE:
<223> OTHER INFORMATION: dsDNA reverse

<400> SEQUENCE: 4
gaggtaatta cacg                                                      14

<210> SEQ ID NO 5
<211> LENGTH: 32
<212> TYPE: DNA
<213> ORGANISM: Artificial Sequence
<220> FEATURE:
<223> OTHER INFORMATION: hpDNA1

<400> SEQUENCE: 5
cgtgtaatta cctccagaga ggtaattaca cg                                  32

<210> SEQ ID NO 6
<211> LENGTH: 34
<212> TYPE: DNA
<213> ORGANISM: Artificial Sequence
<220> FEATURE:
<223> OTHER INFORMATION: hpDNA2

<400> SEQUENCE: 6
```

```
cgtgtaatta cctccaggga gaggtaatta cacg                                    34

<210> SEQ ID NO 7
<211> LENGTH: 36
<212> TYPE: DNA
<213> ORGANISM: Artificial Sequence
<220> FEATURE:
<223> OTHER INFORMATION: hpDNA3

<400> SEQUENCE: 7
cgtgtaatta cctccagaag gagaggtaat tacacg                                  36

<210> SEQ ID NO 8
<211> LENGTH: 38
<212> TYPE: DNA
<213> ORGANISM: Artificial Sequence
<220> FEATURE:
<223> OTHER INFORMATION: hpDNA4

<400> SEQUENCE: 8
cgtgtaatta cctccagacc aggagaggta attacacg                                38

<210> SEQ ID NO 9
<211> LENGTH: 28
<212> TYPE: DNA
<213> ORGANISM: Artificial Sequence
<220> FEATURE:
<223> OTHER INFORMATION: hpDNA5

<400> SEQUENCE: 9
cgtaattacc cagaaggagg taattacg                                           28

<210> SEQ ID NO 10
<211> LENGTH: 48
<212> TYPE: DNA
<213> ORGANISM: Artificial Sequence
<220> FEATURE:
<223> OTHER INFORMATION: hpDNA6

<400> SEQUENCE: 10
cgcagtgtaa ttacctcgac cagaaggagt cgaggtaatt acactgcg                     48

<210> SEQ ID NO 11
<211> LENGTH: 46
<212> TYPE: DNA
<213> ORGANISM: Artificial Sequence
<220> FEATURE:
<223> OTHER INFORMATION: DNA aptamer specific for EN2 (Engrailed-2)
<220> FEATURE:
<221> NAME/KEY: misc_feature
<222> LOCATION: (1)..(1)
<223> OTHER INFORMATION: 5' thiol

<400> SEQUENCE: 11
aaaaaaaaaa cgcataatta cctccagaag gagaggtaat tatgcg                       46
```

DNA APTAMER SPECIFICALLY BINDING TO EN2 (ENGRAILED-2) AND USE THEREOF

STATEMENT REGARDING GOVERNMENT RIGHTS

The present invention was made with the support of the Ministry of Science, ICT and Future Planning for Project #2014029297 of the National research lab program.

CROSS-REFERENCE TO RELATED APPLICATION

This application claims priority to and the benefit of Korean Patent Application No. 2014-0188124, filed on Dec. 24, 2014, the disclosure of which is incorporated herein by reference in its entirety.

BACKGROUND

1. Field of the Invention

The present invention relates to a DNA aptamer specifically binding to EN2 (Engrailed-2), a biosensor for diagnosing prostate cancer having the same and a method of diagnosing prostate cancer.

2. Discussion of Related Art

Prostate cancer is the most common cancer in men, and 30% of men aged over 50 years are estimated to be diagnosed with prostate cancer. According to a plurality of cases of clinical evidence, prostate cancer is considered to have bone metastasis, and it is known that an androgen-dependent state inevitably progresses to an androgen-insensitive state which results in an increase in the death rate of patients. Furthermore, since prostate cancer recurred in about 25% of men who had undergone prostate cancer treatments, additional treatments are required. Currently, prostate cancer is the second cause of cancer death in men in the USA, and early diagnosis and treatments therefor are necessary.

Direct methods among currently used prostate cancer diagnostic methods include a prostate direct illumination method of and a biopsy. When diagnosis is performed using the direct illumination method or the biopsy, it is difficult to diagnose the onset of prostate cancer at an early stage. Therefore, the development of a method that can be used to perform early in vitro diagnosis is urgent.

Indirect methods include a diagnostic method that can be used to perform in vitro examination using a prostate-specific antigen (PSA) test. However, PSAs used for diagnosis are generated not only in malignant prostate epithelial tissues but also in the normal and benign cells, which causes a high false positive rate in prostate cancer detection. Also, when a serum PSA level is very high, the PSA test can be used as an effective standard diagnostic method of prostate cancer. However, when the PSA serum level is low, for example, 2-10 ng/mL, it is difficult to perform reliable prostate cancer diagnosis. As described above, when a PSA concentration is low, the serum PSA can be produced from non-tumor diseases such as benign prostatic hyperplasia (BPH), prostatitis or other physical injuries. Therefore, PSA analysis for prostate cancer diagnosis has a detection specificity problem.

Therefore, diagnosis of prostate cancer using a new biomarker has become a main object, and research thereon has been conducted (Korean Patent No. 10-2009-0111307), but there is much to be desired.

SUMMARY OF THE INVENTION

In view of the above-described problems, a specific binding ability of a DNA aptamer prepared according to the present invention with respect to EN2 (Engrailed-2) proteins was identified and the present invention has been completed based on the identification.

The present invention is provided to develop a DNA aptamer specifically binding to EN2 and provides a DNA aptamer having a nucleotide sequence selected from among SEQ ID NOs 5 to 10.

The present invention also provides a biosensor for diagnosing prostate cancer including an EN2 (Engrailed-2)-specific DNA aptamer and a substrate to which the DNA aptamer is fixed, wherein the DNA aptamer has a nucleotide sequence selected from among SEQ ID NOs 5 to 10.

The present invention also provides a method of diagnosing prostate cancer including: (1) an operation in which a subject sample is treated with the DNA aptamer; and (2) an operation in which a level of EN2 bound to the DNA aptamer is measured.

However, the scope of the present invention is not limited to the above-described objects, and other unmentioned objects may be clearly understood by those skilled in the art from the following descriptions.

In view of the above-described objects, the present invention provides a DNA aptamer that specifically binds to EN2 (Engrailed-2) and has a nucleotide sequence selected from among SEQ ID NOs 5 to 10.

The present invention also provides a prostate cancer diagnostic composition including the DNA aptamer.

The present invention also provides a biosensor for diagnosing prostate cancer including an EN2 (Engrailed-2)-specific DNA aptamer and a substrate to which the DNA aptamer is fixed, wherein the DNA aptamer has a nucleotide sequence selected from among SEQ ID NOs 5 to 10.

As one implementation example of the present invention, the substrate may include a metallic electrode layer and a metallic nanoparticle layer, and the metal may be gold (Au).

As another implementation example of the present invention, the biosensor may further include a linker between the substrate and the DNA aptamer.

The present invention also provides a method of diagnosing prostate cancer including: (1) an operation in which a subject sample is treated with the DNA aptamer; and (2) an operation in which a level of EN2 bound to the DNA aptamer is measured.

The present invention also provides diagnostic use of prostate cancer of a composition containing a DNA aptamer specifically binding to EN2 (Engrailed-2).

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
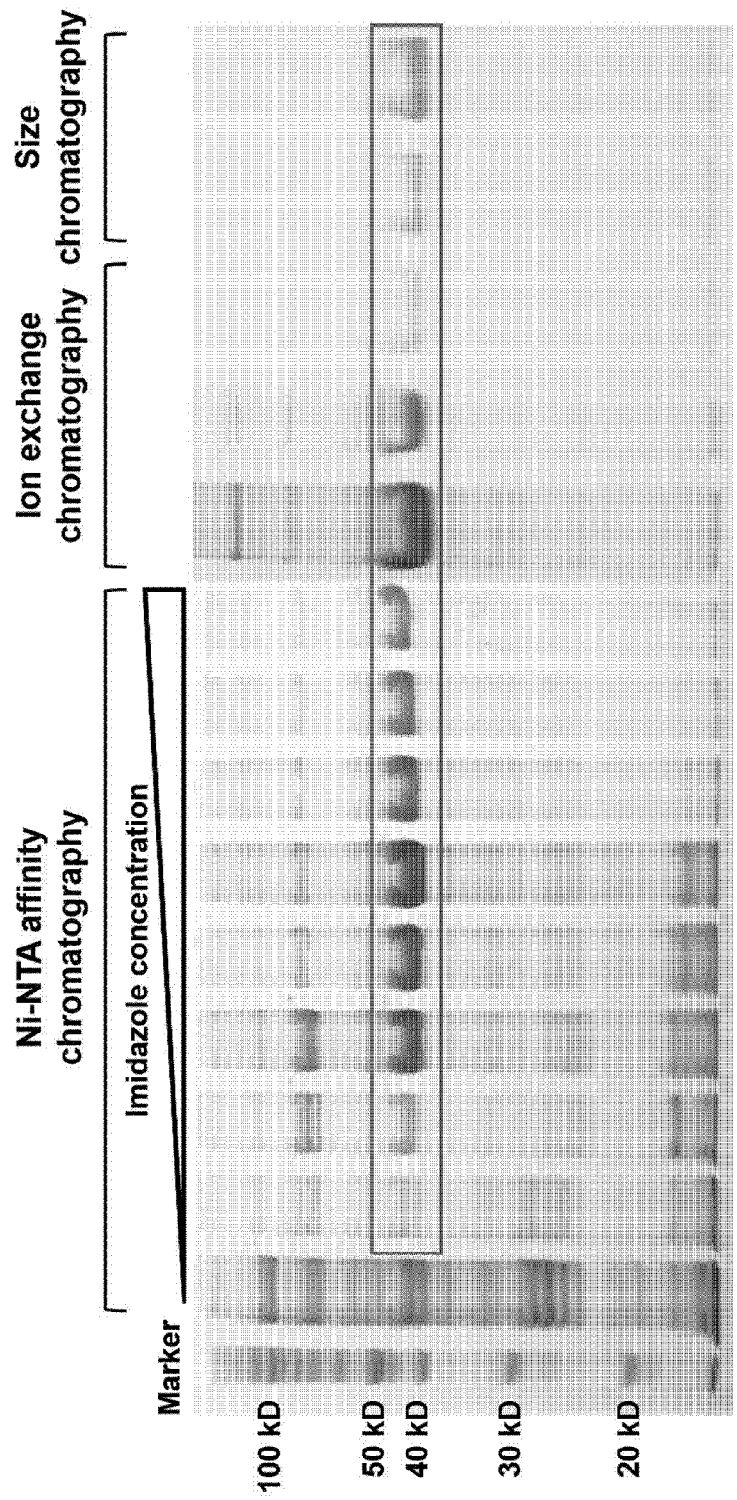
FIG. 1 shows the result of identified EN2 proteins according to Ni-NTA chromatography, ion exchange chromatography, and size chromatography.

The inventors prepared a DNA aptamer having a hairpin structure based on double-stranded DNA (dsDNA) having a strong binding ability with respect to EN2 and a biosensor using the same, identified a strong binding force and excellent specificity of the DNA aptamer and the biosensor with respect to EN2, and completed the present invention based on the identification.

Hereinafter, the present invention will be described in detail.

The present invention provides a DNA aptamer specifically binding to EN2 (Engrailed-2).

In the present invention, the term "EN2 (Engrailed-2)" is one of the biomarkers that can address a detection specificity problem of a prostate-specific antigen (PSA) test used for prostate cancer diagnosis of the related art. An EN2 protein serves as a transcription factor in a cell, is overexpressed in a prostate cancer cell, and causes a DNA transcription control failure. Furthermore, when EN2 expression increases in prostate cancer cells, an amount of EN2 proteins excreted in the urine also increases, which is appropriate for in vitro analysis. Therefore, it is possible to effectively diagnose prostate cancer through EN2 protein detection.

The term "aptamer" used herein refers to single-stranded DNA (ssDNA) or RNA having a high specificity and affinity with respect to a specific material. Methods using developed antibodies have problems in that, since a biological immune system is used, it requires relatively much time and cost, and since the antibody is a protein, a stability problem occurs. On the other hand, since the aptamer is synthesized using a relatively simple method, and cells, proteins and small organic materials can be a target material, new detecting methods using the same can be developed, and its specificity and stability are higher than those of the developed antibodies. In view of such advantages, the DNA aptamer was used for specific detection of the EN2 protein. Preferably, the aptamer may have a nucleotide sequence of SEQ ID NOs 5 to 10, but the present invention is not limited thereto.

The present invention also provides a prostate cancer diagnostic composition including the DNA aptamer.

The composition of the present invention may further include a pharmaceutically and physiologically acceptable carrier, forming agent, and diluent in addition to the DNA aptamer. Exemplary carriers, excipients and diluents that can be appropriately included in the composition may include lactose, dextrose, sucrose, sorbitol, mannitol, xylitol, erythritol, maltitol, starches, acacia rubber, alginate, gelatin, calcium phosphate, calcium silicate, cellulose, methyl cellulose, amorphous cellulose, polyvinylpyrrolidone, water, methyl hydroxybenzoate, propyl hydroxybenzoate, talc, magnesium stearate, mineral oil, etc. When the composition is made into a medicinal compound, a general filler, extending agent, bonding agent, disintegrating agent, surfactant, anti-clumping agent, lubricant, wetting agent, flavoring, emulsifying agent, preservative, etc. may be further included.

The present invention also provides a biosensor for prostate cancer diagnosis including an EN2-specific DNA aptamer and a substrate to which the DNA aptamer is fixed.

The substrate to which the DNA aptamer is fixed according to the present invention includes a metallic electrode layer and a metallic nanoparticle layer. The electrode layer and the nanoparticles may be made of any material that can be attracted by an electric or magnetic field and change characteristics of the electric field, and preferably made of gold (Au), but the present invention is not limited thereto.

Also, the biosensor may further include a linker between the substrate and the DNA aptamer in order to improve specific binding to EN2. The linker may have 5 to 15 nucleotide sequences, and preferably 10 nucleotide sequences, but the present invention is not limited thereto.

In an example of the present invention, the EN2 protein was expressed and purified, and a specific binding sequence of 5'-TAATTA-3' was identified (refer to Examples 1 to 3). A strong binding ability of dsDNA having the specific binding sequence with respect to the EN2 protein was identified (refer to Examples 4 and 5). Also, a DNA aptamer and biosensor having an improved stability and binding ability were prepared based on the above experiment result (refer to Examples 6 and 7). Since the biosensor has a very excellent binding specificity with respect to the EN2 protein, the biosensor was identified to be used as an information providing method for prostate cancer diagnosis (refer to Example 8).

The present invention provides a method of diagnosing prostate cancer including: (1) an operation in which a subject sample is treated with the DNA aptamer; and (2) an operation in which a level of EN2 bound to the DNA aptamer is measured.

Hereinafter, exemplary examples of the invention will be described for promoting an understanding of the invention. However, the following examples should be considered in a descriptive sense only and the scope of the invention is not limited to the following examples.

Example 1

EN-2 Gene Cloning

In order to amplify EN2 genes, a forward primer (5'-CCC GGA TCC ATG GAG GAG AAT GAC CCC AAG C-3' (SEQ ID NO 1)) and a reverse primer (5'-CCC CTC GAG CTA CTC GCT GTC CGA CTT GC-3'(SEQ ID NO 2)) were used.

In order to amplify genes, amplification was performed through a polymerase chain reaction (PCR) process using i-pfu polymerase from cDNA. Operations of the polymerase chain reaction are as follows: 1) an operation in which dsDNA of a template was released for 1 minute at 95° C., 2) an operation in which a primer was bound to the template for 30 seconds at 58° C., and 3) an operation in which a new strand was synthesized and a reaction was performed for 1 minute at 72° C. These operations were repeated 30 times.

The amplified EN2 genes were cloned in a pET28a vector, which is a vector containing $(His)_6$-tag, through a restriction enzyme digestion reaction and a DNA ligation reaction, and the vector was used for BL21(DE3) *E. coli* transformation.

Example 2

Expression of EN-2 Protein

BL21 (DE3) cells in which EN2 genes were transformed were cultured in a Luria Bertani (LB) medium at 37° C. Then, in order to induce expression of proteins, isopropyl-thio-b-D-galactopyranoside (IPTG) was added to have a final concentration of 0.1 mM, and then cultured for 4 hours at 37° C. Expression of the protein was identified through gel electrophoresis, and cells were separated from the medium using a high-speed centrifuge, and washed with a PBS (10 mM sodium phosphate, 150 mM NaCl, and pH 7.4) buffer once.

Example 3

Purification of EN-2 Protein

In order to purify the EN2 protein expressed in the bacteria cell BL21 (DE3) at a high purity, cells were lysed in a cell lysis buffer (20 mM Tris, 500 mM NaCl, 0.5 mM β-mercaptoethanol, 3% glycerol, 0.01% Tween 20, and pH 8.0), and were then destroyed according to sonication for 15 minutes using a sonicator. Centrifuging was performed in order to separate proteins and cells in an aqueous solution.

Also, in order to obtain proteins of a high purity, a characteristic in which Ni-NTA (Ni-nitrilotriacetic acid) and $(His)_6$-tag amino acids bind was used. Specifically, as shown in FIG. 1, since a $(His)_6$-tag of proteins adsorbed to an Ni-NTA column competitively adsorbs with an imidazole compound, when a concentration of imidazole was sequentially increased, EN2 proteins of 40 kD were separated at a high purity.

However, since a protein sample purified using the Ni-NTA column may have a great amount of impurities, additional purification was performed. Therefore, a MonoQ column, which is an ion exchange column through which separation is performed according to a pI value of the protein, was used to perform purification once again. Then, a Superdex 200 column, which is a gel filtration column through which separation is performed according to a size of the protein, was used to perform separation once again, and a purity was increased to 95% or more.

Example 4

Measurement of EN-2 Binding

It was identified that the EN2 protein serving as a transcription factor had a specific binding sequence of 5'-TAATTA-3.' The inventors tried to design an EN2-specific DNA aptamer using dsDNA having the specific binding sequence. Before the design, it was evaluated whether EN2 can bind to the specific binding sequence of 5'-TAATTA-3,' and an electron mobility shift assay (EMSA) and surface plasmon resonance (SPR) were performed.

Specifically, in the EMSA, a solution in which the EN2 protein and dsDNA having a specific binding sequence were contained was reacted for 30 minutes, and then, gel electrophoresis (100 V, 50 min) was performed. Also, in the SPR, the EN2 protein fixed to an NTA chip was reacted with a solution in which dsDNA having a specific binding sequence was contained, and then a resonance wavelength-shift according to a composition change of a material was observed. Therefore, it was measured whether binding to the EN2 protein was performed.

Figure 2:
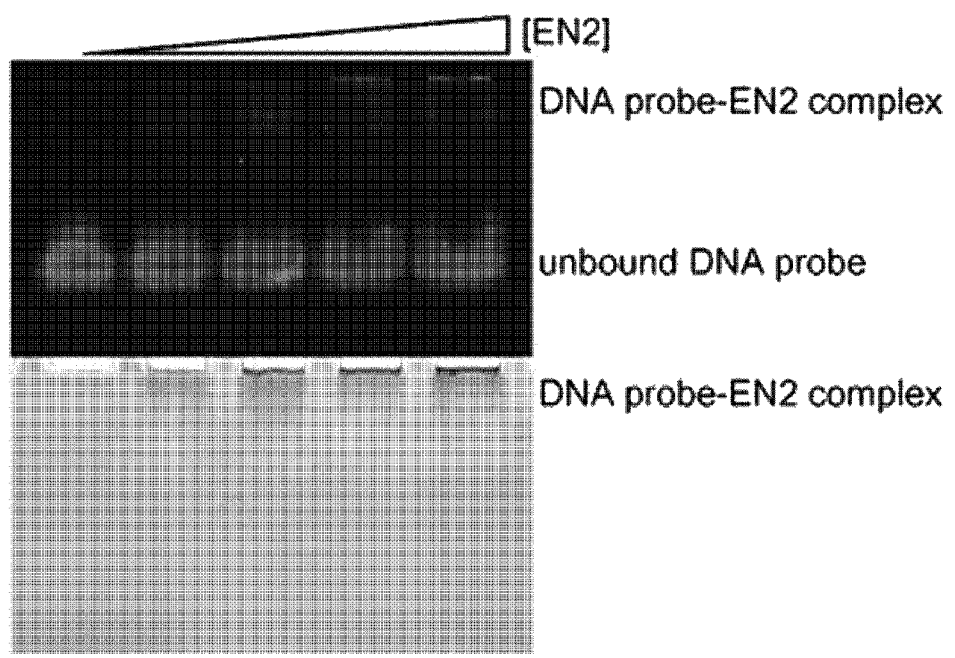
FIG. 2 shows the identified result regarding whether EN2 proteins bind to double-stranded DNA (dsDNA) having a specific binding sequence through an electrophoretic mobility shift assay (EMSA)
Figure 3:
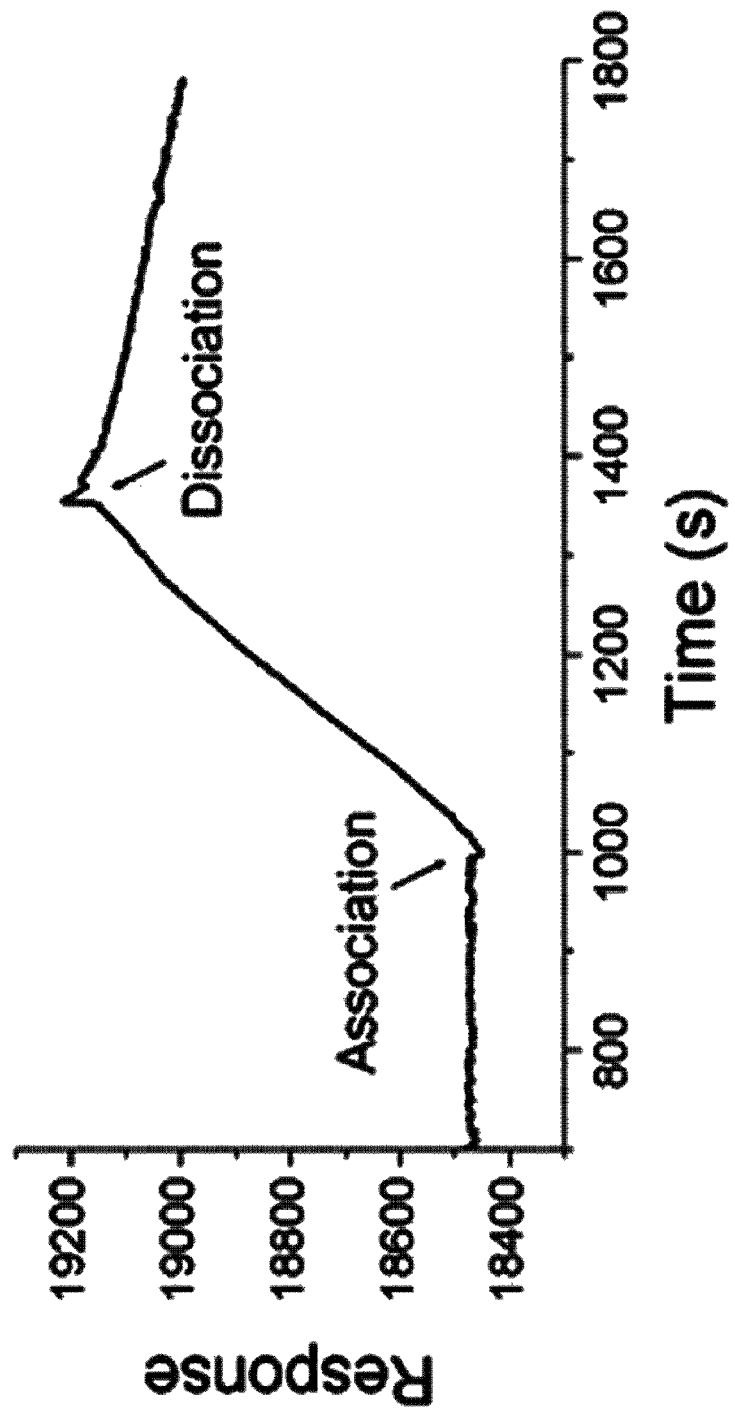
FIG. 3 shows the identified result regarding whether EN2 proteins bind to dsDNA having a specific binding sequence through surface plasmon resonance (SPR)

As a result, as shown in FIG. 2, a decrease in a movement speed due to binding of dsDNA and the EN2 protein was identified. As an EN2 concentration increases, a significant decrease in the movement speed was identified. Also, as shown in FIG. 3, in the SPR, an increase (association phase) of an SPR signal due to binding of dsDNA and the EN2 protein was identified, and a slow decrease (dissociation phase) of the SPR signal increased according to strong binding between dsDNA and the EN2 protein was identified. The result shows that dsDNA having a sequence of 5'-TAATTA-3 strongly binds to the EN2 protein.

Example 5

Measurement of EN-2 Binding Force Through Fluorescence Measurement

In order to identify whether quantitative analysis through a dsDNA probe is possible, fluorescent analysis using a SYBR Green I (SGI) fluorescent dye was performed. When there is no EN2 protein, SGI binds to the dsDNA probe and generates a fluorescent signal. On the other hand, when there is the EN2 protein, the dsDNA probe binds to the EN2 protein, and binding of SGI decreases. In the present example, SGI spectrums at various EN2 concentrations (1 nM to 100 nM) were analyzed and thereby fluorescent signal decreases were compared.

Figure 4:
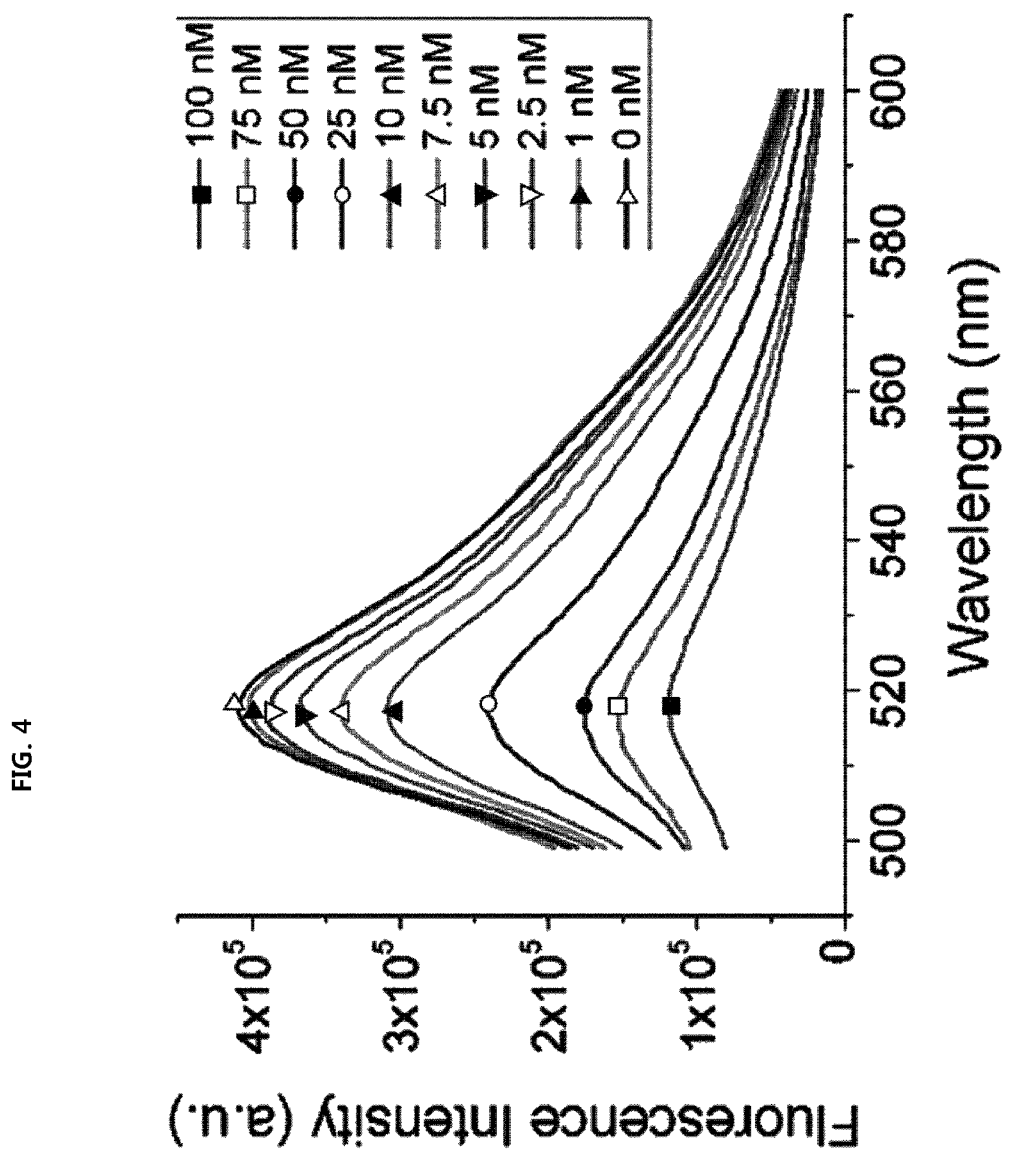
FIG. 4 shows the identified result regarding whether binding to a dsDNA probe is performed according to EN2 protein concentrations (1 nM to 100 nM) through a SYBR Green I (SGI) spectrum.
Figure 5:
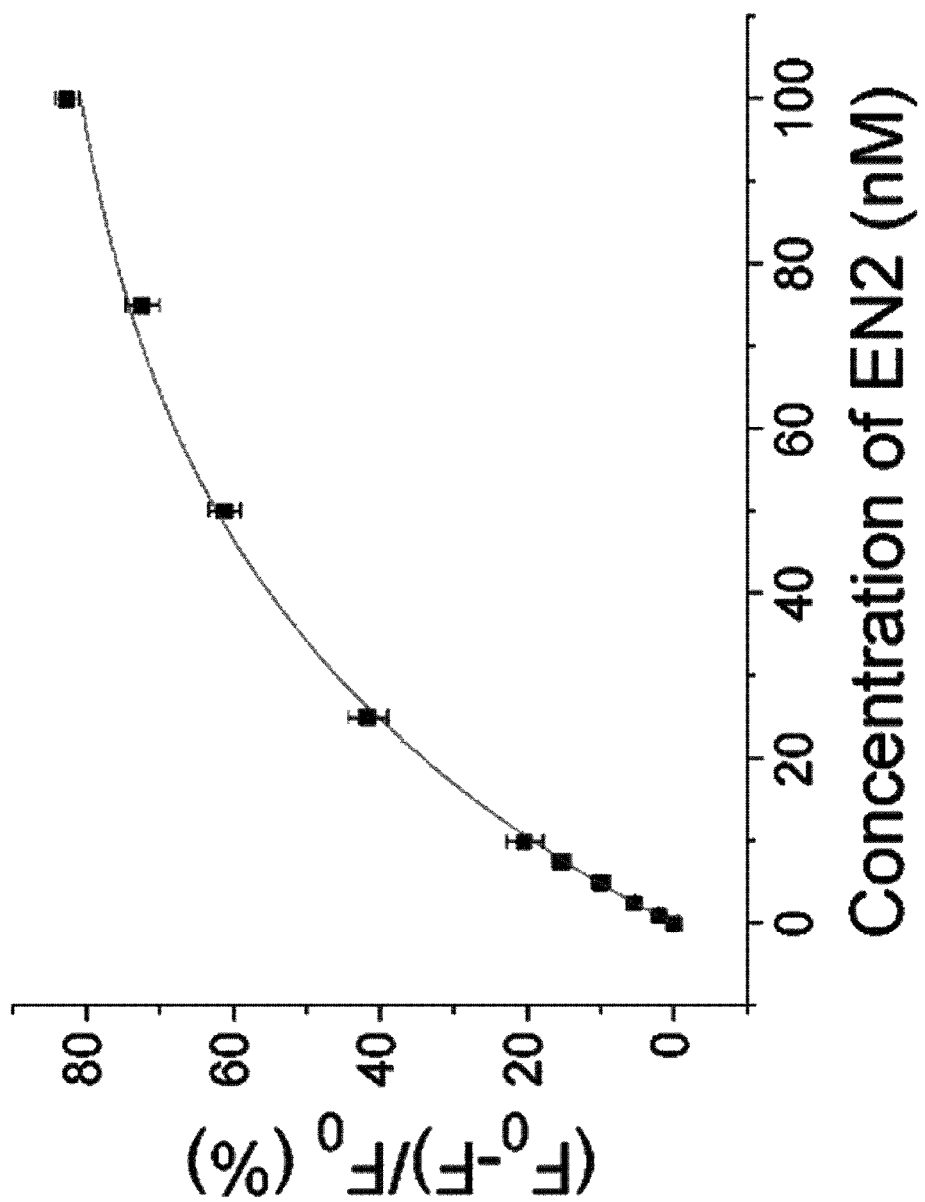
FIG. 5 shows the numerical result of a decrease of a fluorescent signal due to binding to a dsDNA probe according to EN2 protein concentrations (1 nM to 100 nM)

As a result, as shown in FIGS. 4 and 5, comparing a control group (0 nM), it was identified that the fluorescent signal also decreases as the EN2 concentration increases. The result indicates that quantitative analysis for EN2 specific detection using the dsDNA probe of the present invention is possible.

Example 6

Preparation of DNA Aptamer Having Improved Stability and Binding Strength

Figure 6:
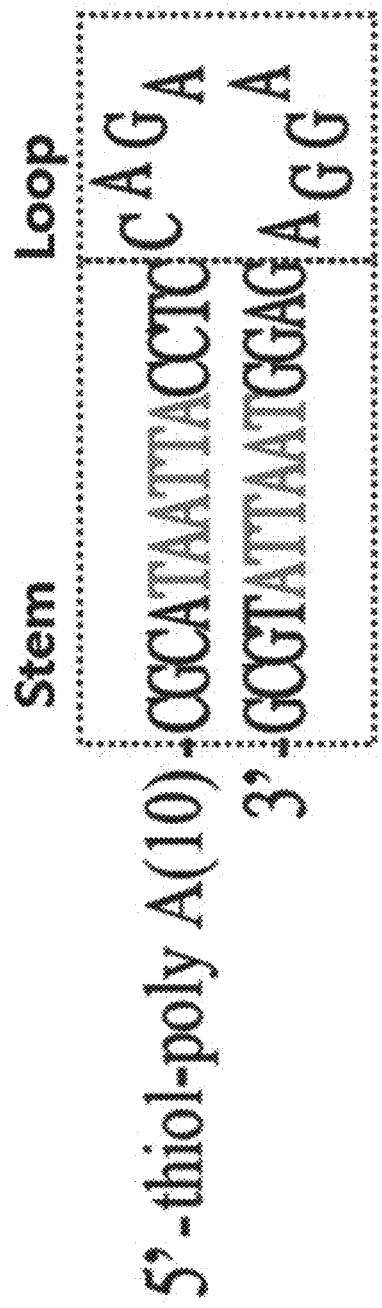
FIG. 6 shows a secondary structure of a DNA aptamer specifically binding to EN2 (Engrailed-2)

In order to improve a stability of EN2 protein detection and a binding strength, a DNA aptamer having a hairpin structure was designed. As shown in FIG. 6, the DNA aptamer has a loop part and a stem part, and DNA aptamers (hpDNA1, hpDNA2, hpDNA3, hpDNA4, hpDNA5, and hpDNA6) having different lengths of loop parts and stem parts were prepared.

Then, in order to compare binding strengths between the EN2 protein and each of the DNA aptamers, a dissociation constant ($K_d$) between the EN2 protein and each of the DNA aptamers was measured. In this case, fluorescein amidite (FAM) was attached to the DNA aptamer as a marker, and an amount of the DNA aptamer bound to the protein was measured according to a fluorescent signal of FAM.

As a result, as shown in Table 1, it was identified that the DNA aptamers (hpDNAs) having a hairpin DNA structure had in general, a decreased dissociation constant value compared to dsDNA probes of the related art. In particular, in hpDNA2 and hpDNA3, a dissociation constant value was greatly changed with a difference of 2 bases in the loop part. On the other hand, there was no significant change between hpDNA3 and hpDNA5. In consideration of such results, it was identified that a length of the loop part greatly influences the binding strength of the DNA aptamer. Also, it was identified that hpDNA3, hpDNA5, and hpDNA6 whose loop parts have a length of 8 bases had a lower dissociation constant value than the other DNA aptamers. The result indicates that the DNA aptamer whose loop part has a length of 8 bases is the most stable DNA aptamer in EN2 protein detection.

TABLE 1

| DNA probe | Loop length (bases) | Stem length (bp) | Sequence (5' to 3') | $K_d$ (nM) |
|---|---|---|---|---|
| dsDNA | 0 | 14 | 5'-CGT GTA ATT ACC TC-3' (SEQ ID NO 3) 5'-GCA CAT TAA TGG AG-5' (SEQ ID NO 4) | 95.22 ± 15.19 |
| hpDNA1 | 4 | 14 | 5'-CGT GTA ATT ACC TCC AGA GAG GTA ATT ACA CG-3' (SEQ ID NO 5) | 85.72 ± 11.09 |
| hpDNA2 | 6 | 14 | 5'-CGT GTA ATT ACC TCC AGG GAG AGG TAA TTA CAC G-3' (SEQ ID NO 6) | 98.84 ± 14.38 |
| hpDNA3 | 8 | 14 | 5'-CGT GTA ATT ACC TCC AGA AGG AGA GGT AAT TAC ACG-3' (SEQ ID NO 7) | 66.33 ± 6.88 |
| hpDNA4 | 10 | 14 | 5'-CGT GTA ATT ACC TCC AGA CCA GGA GAG GTA ATT ACA CG-3' (SEQ ID NO 8) | 88.83 ± 11.82 |
| hDNA5 | 8 | 10 | 5'-CGT AAT TAC CCA GAA GGA GGT AAT TAC G-3' (SEQ ID NO 9) | 68.80 ± 5.42 |
| hpDNA6 | 8 | 20 | 5'-CGC AGT GTA ATT ACC TCG ACC AGA AGG AGT CGA GGT AAT TAC ACT GCG-3' (SEQ ID NO 10) | 61.03 ± 6.52 |

Example 7

Detection Condition Optimization and Biosensor Preparation

Figure 7:
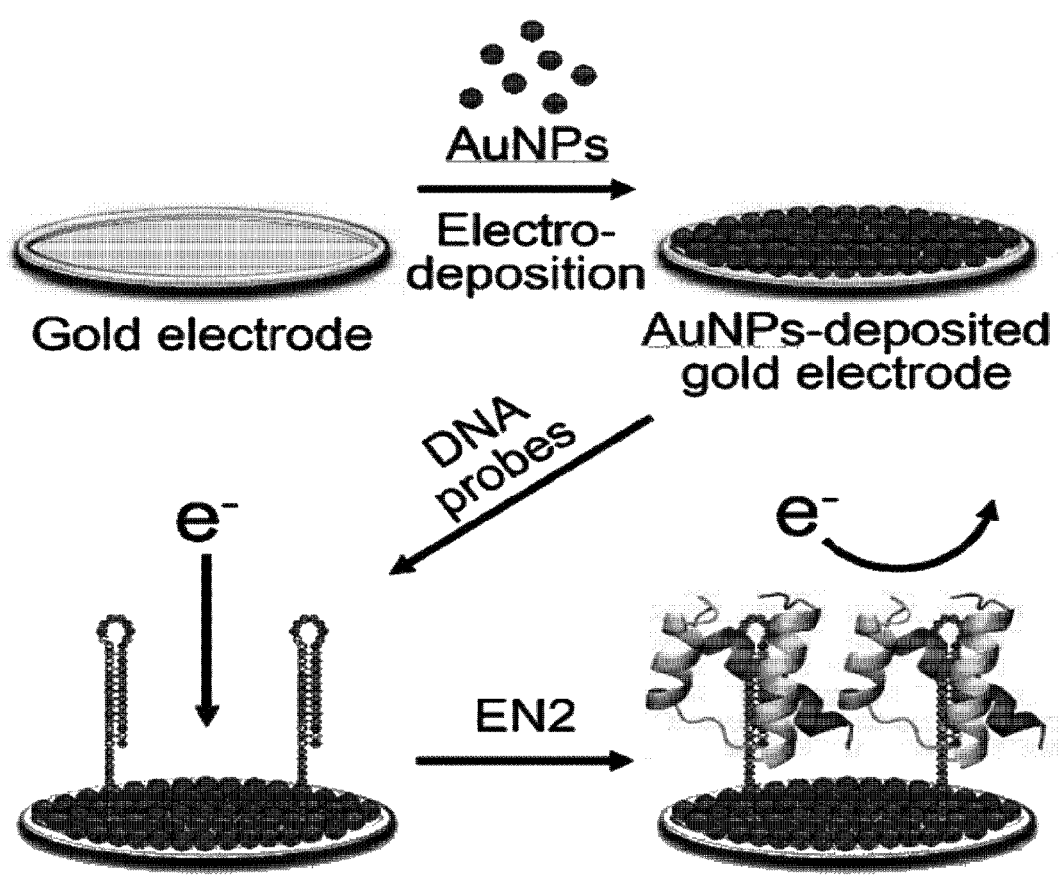
FIG. 7 is a diagram schematically illustrating a method of preparing a biosensor for EN2 protein detection using a DNA aptamer.

Electrochemical impedance spectroscopy (EIS) technology was used to design a biosensor having excellent detection sensitivity. As shown in FIG. 7, first, gold nanoparticles were adsorbed to a gold electrode, the DNA aptamer bound to the electrode, and thereby a biosensor for EN2 detection was prepared.

When the EN2 protein binds to the sensor, an electron flow is blocked and an impedance value increases. Using such a property, preparation of the biosensor optimized for EN2 detection was tried. Specifically, in order to increase selectivity and detection sensitivity, changes in impedance values according to changes in loop lengths and stem lengths of DNA aptamers, and a linker length between a gold surface and the DNA aptamer were measured.

Also, the biosensor including an optimized aptamer in the example was used to identify whether quantitative detection of the EN2 protein is possible.

Figure 8:
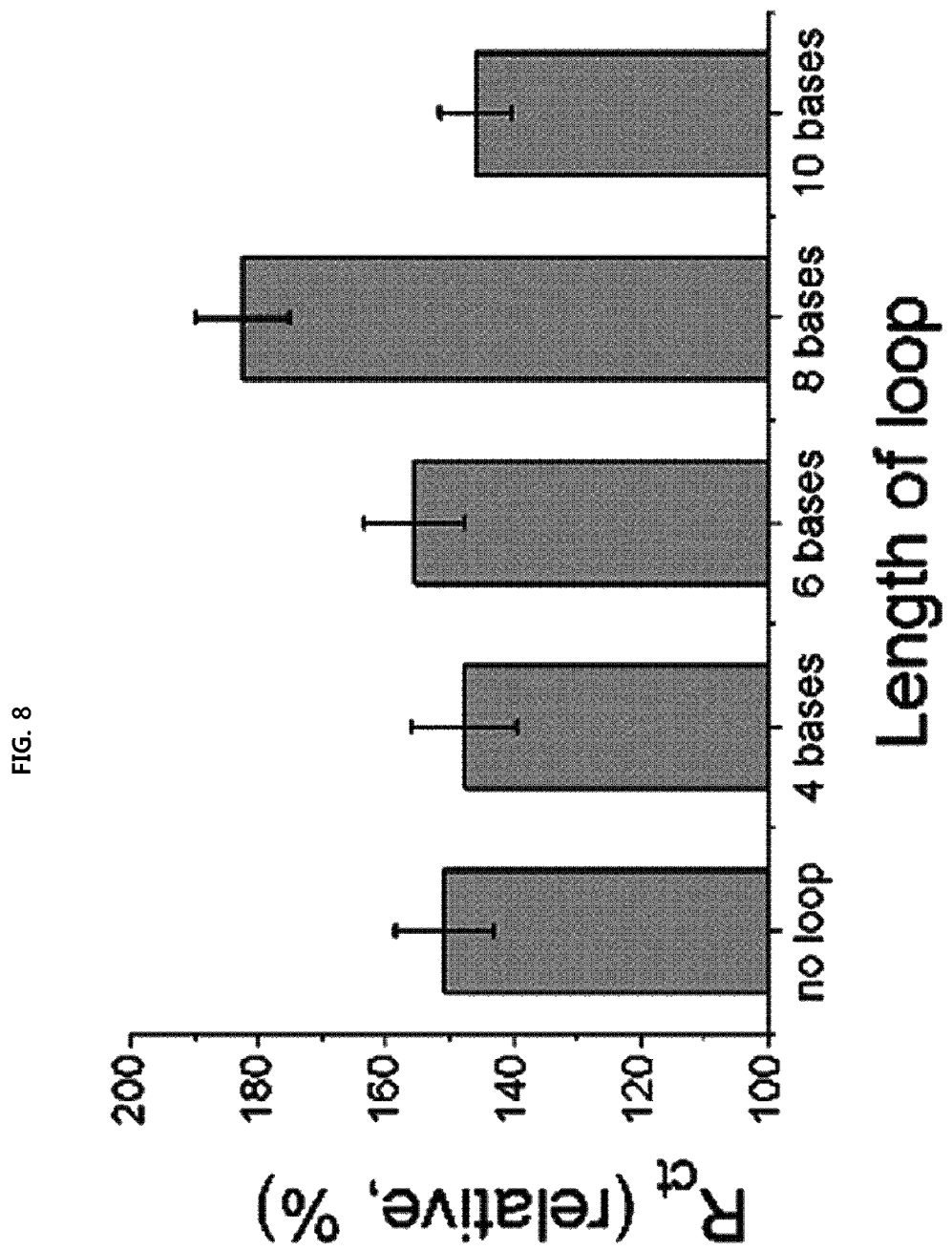
FIG. 8 shows the result of a change in impedance values according to a loop length of a DNA aptamer in a biosensor for EN2 protein detection.
Figure 9:
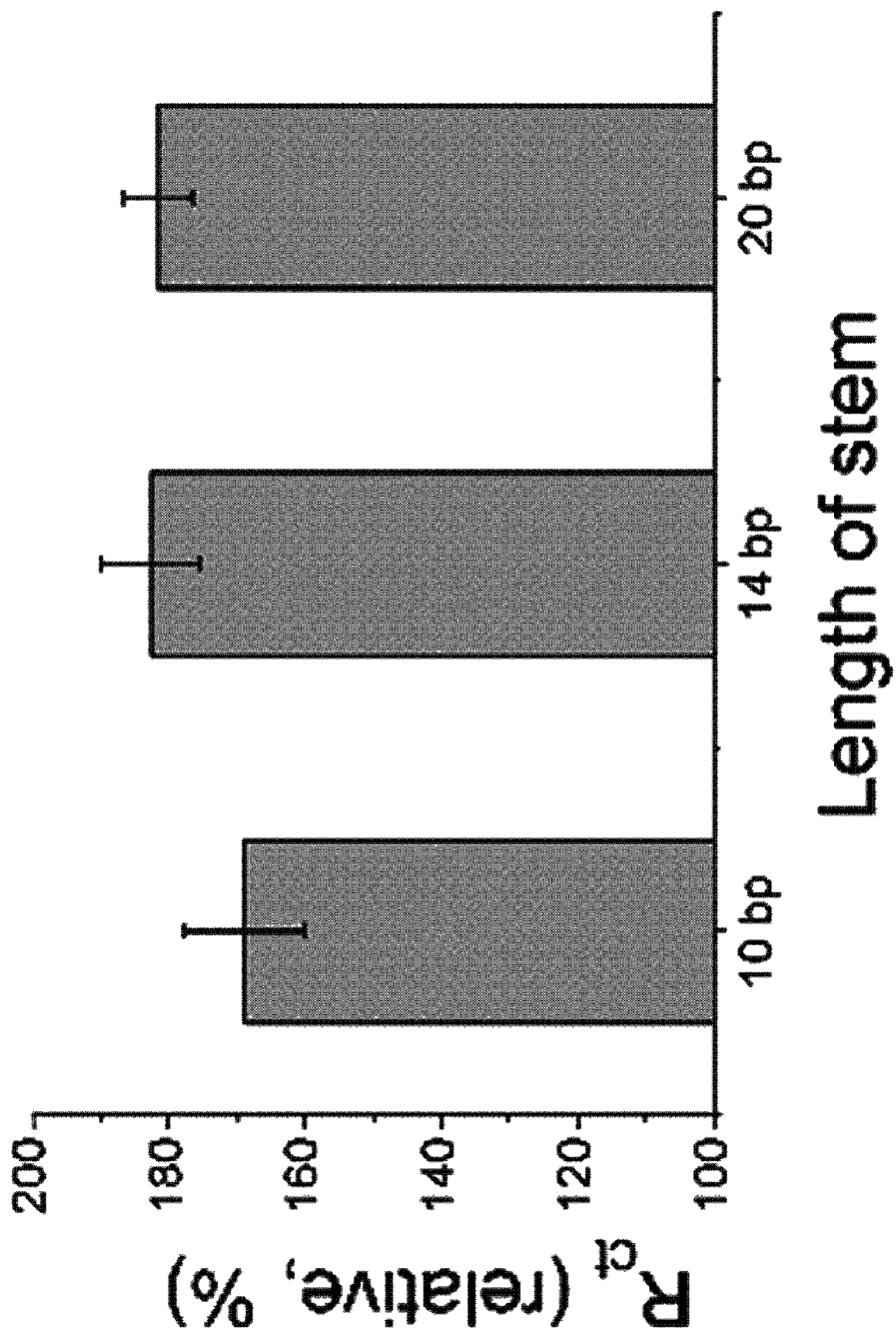
FIG. 9 shows the result of a change in impedance values according to a stem length of a DNA aptamer in a biosensor for EN2 protein detection.
Figure 10:
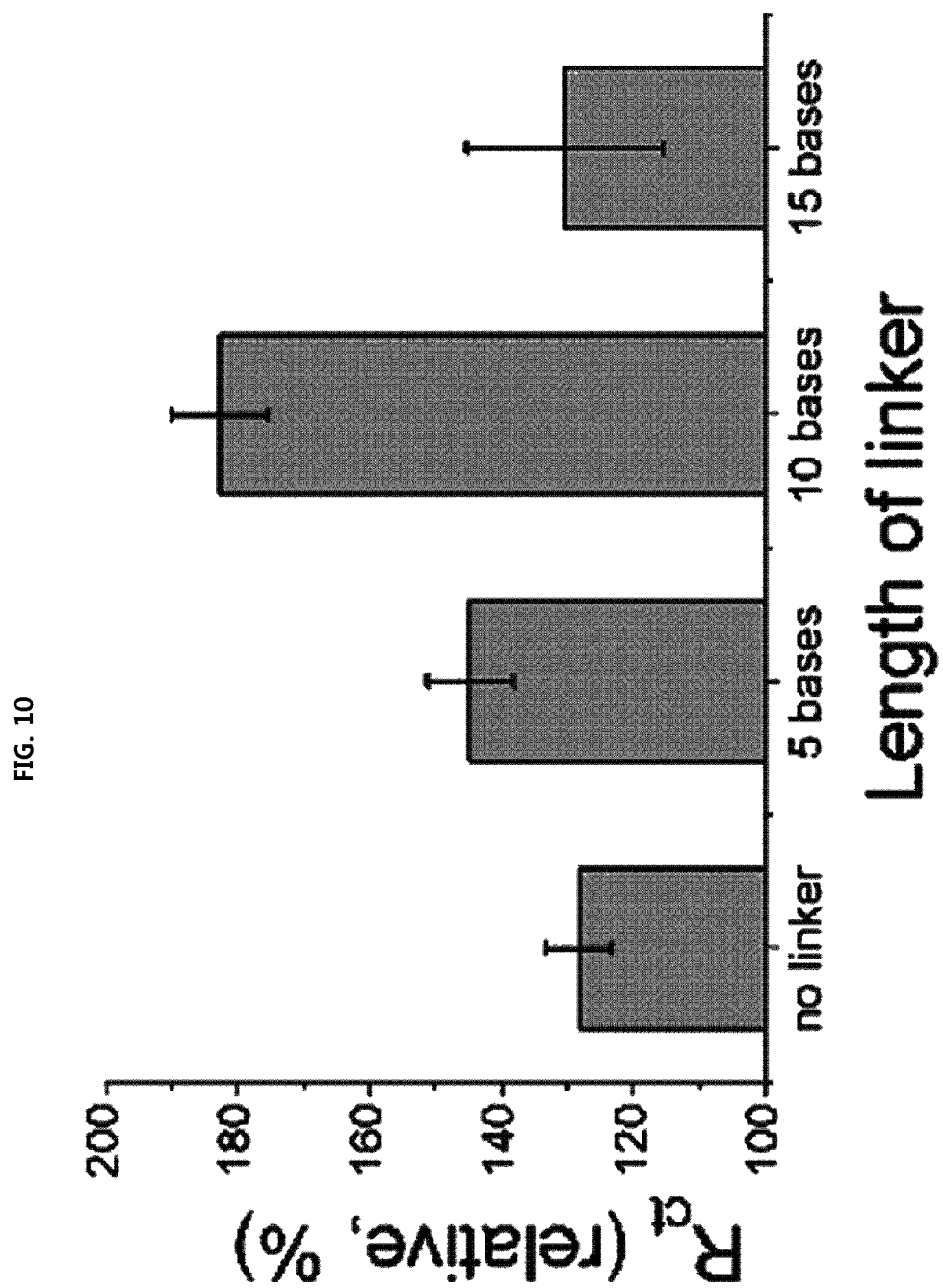
FIG. 10 shows the result of a change in impedance values according to a linker length between a gold surface and a DNA aptamer in a biosensor for EN2 protein detection.

As a result, as shown in FIGS. 8 to 10, it was identified that, when the loop part has a length of 8 bases and the stem part has a length of 14 bases (hpDNA3), the impedance value is the highest, which indicates binding of the greatest amount of EN2 proteins. Based on such identification, similarly to Example 6, it was identified that hpDNA3 whose loop part has a length of 8 bases had a high binding force and a stable sequence. Also, it was identified that the most appropriate length of a linker part connecting to the gold surface and having a poly A sequence was 10 bases.

Figure 11:
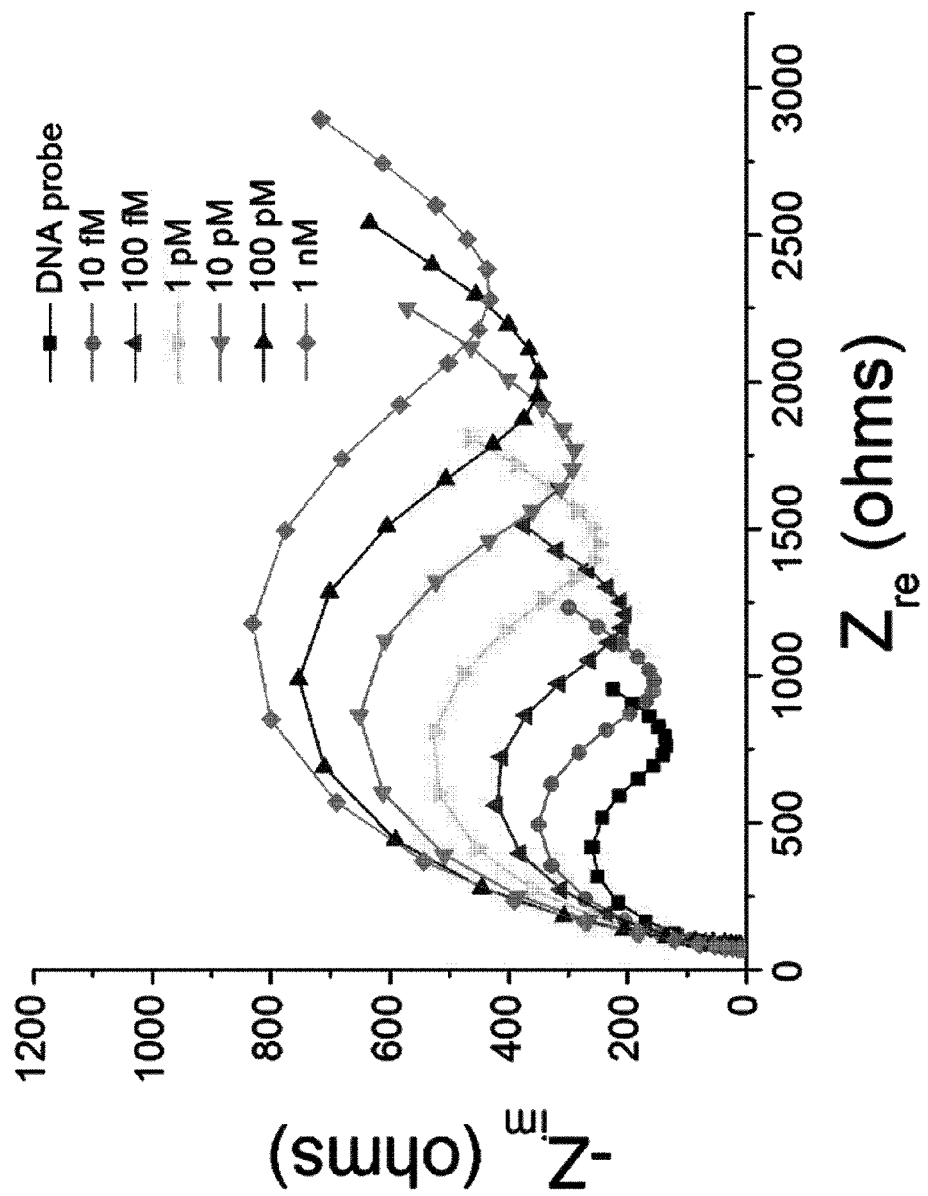
FIG. 11 shows the result of a change in impedance values according to EN2 protein concentrations (1 nM to 100 nM) in a biosensor for EN2 protein detection including an hpDNA3 aptamer.
Figure 12:
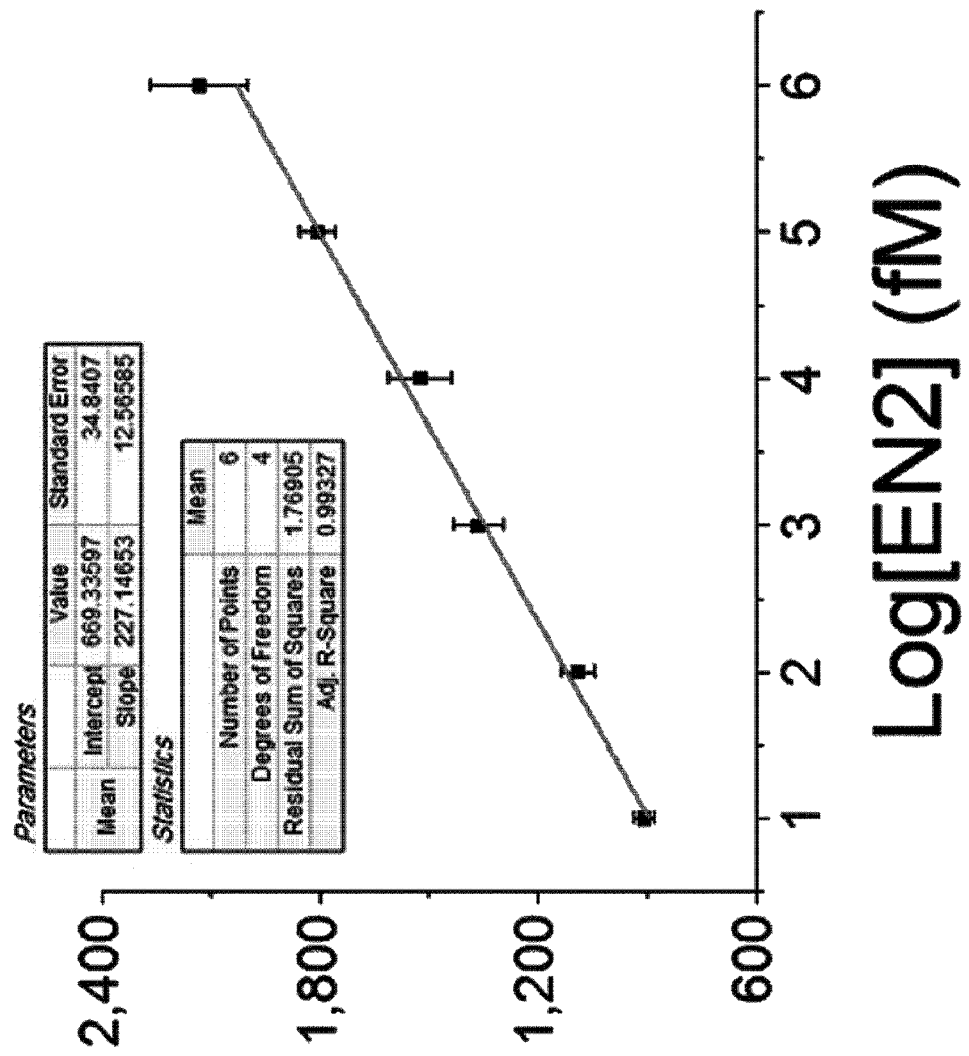
FIG. 12 shows the result of a change in impedance values according to a log value of EN2 protein concentrations in a biosensor for EN2 protein detection including an hpDNA3 aptamer.

Also, based on the result, the hpDNA3 aptamer selected according to optimized conditions was used to detect the EN2 protein. As a result, as shown in FIG. 11, in a Nyquist plot, it was identified that the impedance value increased as the EN2 concentration increased (10 fM to 1 nM). As shown in FIG. 12, it was identified that EN2 was quantitatively detected and a detection limitation was 5.62 fM.

Example 8

Identification of EN2 Binding Specificity

In order to identify selective binding of the DNA aptamer, a binding specificity with respect to several protein samples was identified. Each protein was mixed in an artificial urine medium to have a concentration of 10 pM, and then it was identified whether binding to the DNA aptamer was performed.

Figure 13:
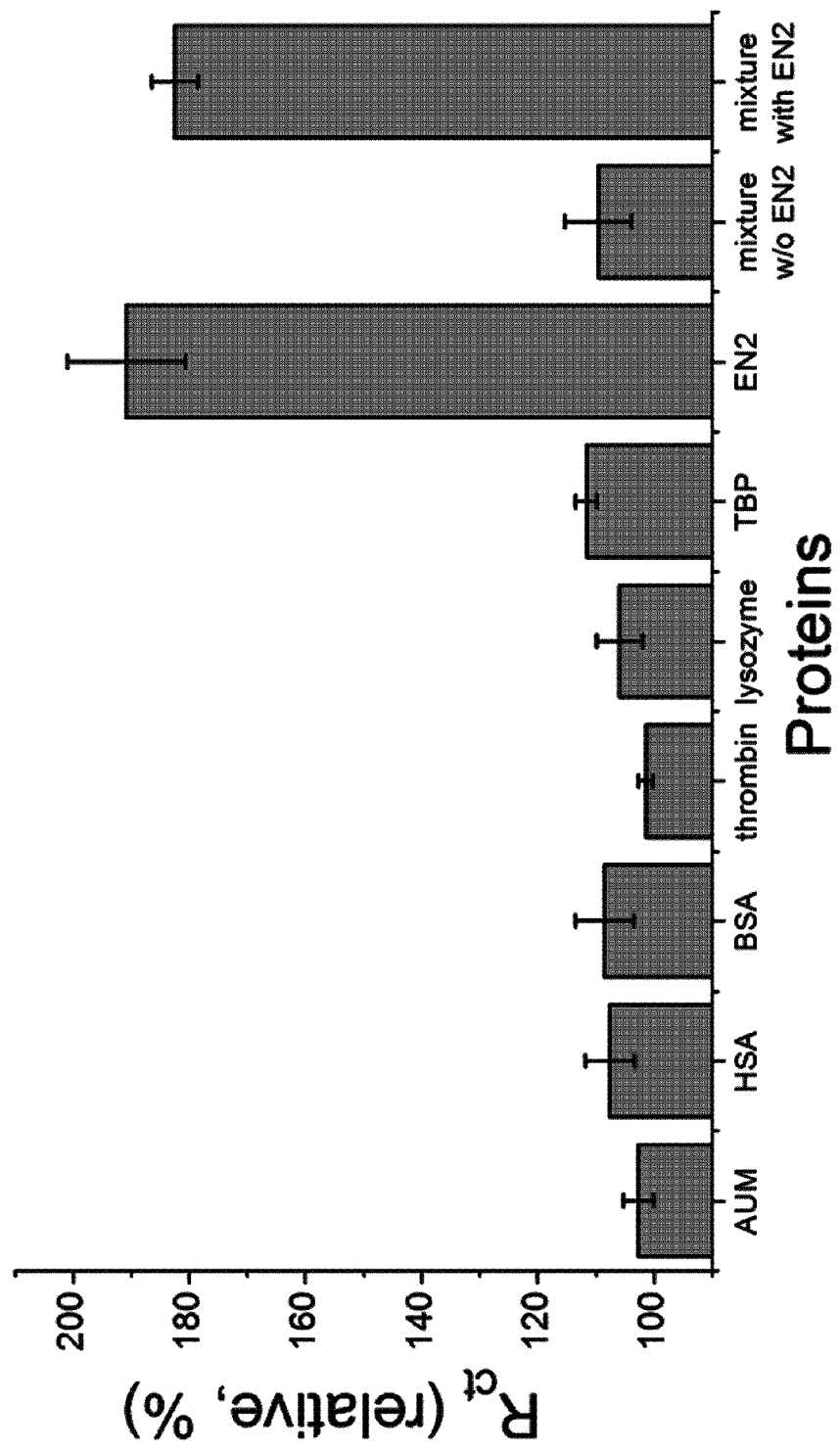
FIG. 13 shows the identified result regarding whether binding among various proteins is performed and binding to EN2 proteins is performed in a mixed solution in a biosensor for EN2 protein detection including an hpDNA3 aptamer using a relative impedance value.

As a result, as shown in FIG. 13, an excellent binding specificity with respect to the EN2 protein was identified. In particular, it was identified that, although a TATA box binding protein (TBP) is a transcription factor that recognizes a homeobox similarly to EN2, it did not bind to the DNA aptamer developed in the present invention. Also, the result shows that, when there was no EN2 in a solution in which several proteins were mixed, no signal is detected, and when EN2 was introduced, the signal was detected.

The result indicates that the DNA aptamer developed in the present invention has a high binding specificity with respect to the EN2 protein and may be used as a biosensor in a complex biological sample.

The composition according to the present invention includes a DNA aptamer specifically binding to EN2 (Engrailed-2) as an active ingredient. A strong binding force and excellent specificity of the DNA aptamer and the biosensor using the same with respect to EN2 proteins were identified.

The composition is expected to be beneficially used as a prostate cancer diagnostic composition that overcomes a detection specificity problem of the prostate-specific antigen (PSA) test in the related art.

The above description of the invention is the only exemplary, and it will be understood by those skilled in the art that various modifications can be made without departing from the scope of the present invention and without changing essential features. Therefore, the above-described examples should be considered in a descriptive sense only and not for purposes of limitation.

What is claimed is:

1. A DNA aptamer specifically binding to EN2 (Engrailed-2) and having a nucleotide sequence selected from among SEQ ID NOs 5 to 10.

2. A biosensor for diagnosing prostate cancer comprising an EN2 (Engrailed-2)-specific DNA aptamer and a substrate to which the DNA aptamer is fixed,
   wherein the DNA aptamer has a nucleotide sequence selected from among SEQ ID NOs 5 to 10.

3. The biosensor for diagnosing prostate cancer according to claim 2,
   wherein the substrate includes a metallic electrode layer and a metallic nanoparticle layer, and the metal is gold (Au).

4. The biosensor for diagnosing prostate cancer according to claim 2,
   wherein the biosensor further includes a linker between the substrate and the DNA aptamer.

5. A method of diagnosing prostate cancer, comprising:
   (1) an operation in which a subject sample is treated with an EN2 (Engrailed-2)-specific DNA aptamer having a nucleotide sequence selected from among SEQ ID NOs 5 to 10; and
   (2) an operation in which a level of EN2 bound to the DNA aptamer is measured.

* * * * *